United States Patent [19]

Deboeck

[11] Patent Number: 4,699,927
[45] Date of Patent: Oct. 13, 1987

[54] ANTICONVULSANT VALPROIC ACID SALTS

[75] Inventor: Arthur M. Deboeck, Herne, Belgium

[73] Assignee: Pharlyse, Luxembourg, Luxembourg

[21] Appl. No.: 864,560

[22] Filed: May 16, 1986

Related U.S. Application Data

[63] Continuation of Ser. No. 794,253, Oct. 30, 1985, abandoned, which is a continuation of Ser. No. 699,507, Feb. 11, 1985, abandoned, which is a continuation of Ser. No. 438,559, Nov. 2, 1982, abandoned.

[30] Foreign Application Priority Data

Nov. 4, 1981 [LU] Luxembourg ............................ 83729

[51] Int. Cl.[4] .................... A61K 31/195; C07D 101/04
[52] U.S. Cl. ................................ 514/564; 260/501.11; 514/565; 548/344; 562/433; 562/553; 562/560; 562/562; 562/606
[58] Field of Search ................ 562/560, 562; 514/564, 514/565; 260/501.11

[56] References Cited

PUBLICATIONS

Kovach, I. et al., *J. Pharm. Sci.*, 64(6), 1070–1071 (1975).
HRC Report: Acute Oral Toxicity of L-Lysine Valproate (Valprolyn Galephar) in the Mouse, Davies, J. et al., Huntingdon Research Centre, Huntingdon, England, 4/27/82.
HRC Report: Acute Oral Toxicity of L-Lysine Valproate (Valprolyn Galephar) in the Rat, Davies, J. et al., Huntingdon Research Centre, Huntingdon, England 4/26/82.
*Chemical Abstracts*, 43:4710a (1949) [Neuberg et al., *Arch. Biochem.*, 19, 149–61 (1948)].
*Chemical Abstracts*, 82:103136w (1975) [Japan. Kokai 74, 81,517, 8/6/74, Kawata].
*Chemical Abstracts*, 91:125092s (1979) [Ger. Offen. 2, 802,195, 7/26/79, Onczul].
*Chemical Abstracts*, 94:36376g (1981) [Ger. Offen. 3,017,032, 11/13/80, Christiansen].
Rohdewald, P. et al., *Thermochimica Acta*, 49, 101–110 (1981).
*Chemical Abstracts*, 89:122899h (1978) [Egli, M. et al., *Schweiz. Rundsch. Med./Prax.*, 1978, 67 (26), 974–80].
Klotz, U. et al., *International Journal of Clinical Pharmacology, Therapy and Toxicology*, vol. 18, No. 10, pp. 461–465 (1980).
Sorel, L. et al., *Acta Neurol. Belg.*, vol. 81, pp. 283–290 (1981) (abstract).

*Primary Examiner*—Richard A. Schwartz
*Attorney, Agent, or Firm*—Marshall, O'Toole, Gerstein, Murray & Bicknell

[57] ABSTRACT

Water-soluble valproic acid salts, consisting of reaction products of valproic acid with at least one basic amino-acid, the latter being preferably selected from the group comprising arginine, lysine, histidine, ornithine and glycine.

9 Claims, No Drawings

ANTICONVULSANT VALPROIC ACID SALTS

This application is a continuation of commonly assigned application Ser. No. 794,253, filed Oct. 30, 1985, now abandoned, which is a continuation of Ser. No. 699,507, filed Feb. 11, 1985, now abandoned, which is a continuation of Ser. No. 438,559 filed Nov. 2, 1982, now abandoned.

This invention relates to pharmaceutically acceptable water-soluble valproic acid salts.

Valproic acid or 2-n-propyl pentanoic acid is a well known drug, more particularly for its anticonvulsant properties. However, it has the drawbacks to be liquid and to be insoluble in water, which impedes its use in most pharmaceutical forms. To prevent said drawbacks, various crystalline forms have been proposed with little success. Valproic acid alkali metal salts have also been provided but the latter, while soluble, and solid have the drawback to bring with themselves, alkaline ions which often are unsuitable, more particularly in long-term treatment of subjects submitted to a sodium-free diet.

This invention has for its object to provide a solid and highly water-soluble valproic acid salt which does not have the drawbacks of the alkali metal salts.

To that purpose, according to the invention, the salt consists of the reaction product of valproic acid with at least one basic amino-acid.

Advantageously, this salt contains about 1 to 5 moles, and preferably about 1 mole of basic amino-acid per mole of valproic acid.

The basic amino-acid or amino-acids used may be natural or not, such as, for example arginine, lysine, histidine, ornithine or glycine. The basic amino-acids according to the invention can include one or more asymetrical centres and in this connection they can exist as optically active isomer forms. It should be clearly understood that the invention includes both the epimer forms, such as the levogyre and dextrogyre forms, as well as mixture thereof. Examples of levogyre and dextrogyre basic amino-acids are D - and L lysines and D - and L - arginines.

The invention also concerns the preparation of said valproic acid salts.

According to a first way of processing, valproic acid is reacted with an aqueous solution containing the amino-acid or amino-acids. After reaction, the excess of acid is removed by washing with an organic solvent, water being then separated from the reaction product so obtained by suitable separation methods, such as by evaporation or lyophilization. Examples of organic solvents are alkanes, alkyl acetates, chlorinated solvents and their mixture.

Another way of proceeding consists of reacting an aqueous, hydroorganic or organic solution or dispersion containing the amino-acid or amino-acids with an organic solution or dispersion containing valproic acid, with an aqueous solution or dispersion containing valproic acid or with valproic acid as it is, and separating the solvent from the reaction mixture so obtained by suitable separation methods, such as by filtration, lyophilization or evaporation. The addition sequence can be reversed. Examples of organic solvents used for dissolving the amino-acids and valproic acid are polar organic solvents, such as alcohols, glycols, polyglycols, ketones, dimethylformamide and dimethylsulfoxide. Mixtures of such solvents can also be used.

A third way of proceeding consists of bringing into contact a salt or salts of the basic amino-acid or amino-acids in aqueous, organic or hydroorganic solution or dispersion with valproic acid as it is or an organic solution of valproic acid and to separate the solvent from the reaction mixture by suitable separation methods, such as by evaporation, lyophilization or filtration. An example of salt of amino-acid is lysine carbonate. Examples of precipitation solvents are alkyl acetates, sulfuric ether, dioxane, tetrahydrofurane, ketones and mixtures thereof.

According to the invention, in all these cases, said treatment is carried out at a temperature of about $-5°$ C. to 100° C., and preferably at a temperature of about 20° C.

Valproic acid is a very slightly water soluble liquid, organic acid. As already above-mentioned, the salts are easily obtained with basic amino-acids, such as arginine, lysine, histidine, ornithine and glycine.

The highly water-soluble salts of valproic acid require between 1 and 5 molecules and preferably 1 molecule of amino-acid per valproic acid molecule.

As a matter of fact, the valproic acid salts of the invention have the following formula:

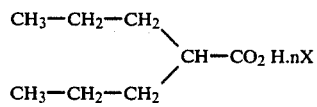

wherein n, being the number of amino-acid molecules per molecule of valproic acid, is comprised between 1 and 5 and preferably is 1 or 2, and X is the aminoacid or the amino-acids.

The hydrosoluble valproic acid salts of the present invention may thus be obtained by using known salt preparation methods, and particularly, by bringing into aqueous, hydro-organic or organic solution or suspension one or several amino-acids, or by bringing into aqueous, hydro-organic or organic solution or suspension one or several amino-acids salts to which, while keeping the temperature between $-5°$ C. and 100° C. and preferably at about 20° C., is added under stirring by small portions the required amount of valproic acid, optionally as organic solution. To this end, it should be noted that the addition sequence of the concerned reactants may be reversed.

When the solution becomes clear, the solvent is removed from the reaction mixture by any suitable separation methods, such as, for example, by filtration (organic or hydro-organic solution), lyophilization (aqueous solution) or by moderate heating under vacuum. A water-soluble powder is so obtained, which may be used for preparing solid forms (tablets, suppositories, lozenges, granules, sugar-coated pills) and injectable forms. It is obvious that the solutions of valproic acid salts, prepared as hereinafter explained, may be used immediately as injectable form without being previously lyophilized, provided that their ionic strength is acceptable or rendered so, as well as their sterility.

Hereinafter some non limitative examples for preparing compounds according to the invention are given.

EXAMPLE 1

To an aqueous solution of 50 ml containing 7.3 g of lysine-base, 7.93 g of valproic acid are added gradually and under stirring. After about one hour of mixing, the aqueous solution is washed with 20 ml of n-hexane. After lyophilization, about 14.50 g of lysine valproate instantaneously water-soluble and having the following characteristics are obtained : pH of a 10% aqueous solution : 7.7–8.5; melting point : 152°–154° C. with decomposition; water-solubility at 20° C. higher than 50%.

By proceeding in the same way with arginine, histidine or ornithine, the corresponding salts which are all instantaneously water-soluble, are obtained.

EXAMPLE 2

To a solution of 14,6 g of lysine-base in 50 ml of water, 14.42 g of valproic acid dissolved in 100 ml of methanol are added by small portions. After a reaction period of about 1 hour, the solution is evaporated to dryness. The so obtained white powder is again dissolved with 50 ml of methanol and after a slow addition under stirring of 250 ml of ethyl acetate, the crystallized salt is filtered off. After drying at 60° C., about 26 g of instantaneously water-soluble lysine valproate are obtained.

EXAMPLE 3

To a suspension of 7.3 g of anhydrous lysine-base in 25 ml of methanol, 7.21 g of valproic acid are added under stirring. When the solution is clear, the latter is added slowly to 150 ml of ethyl acetate under vigorous stirring. The obtained precipitate is filtered off and washed with ethyl acetate. About 13.4 g(92%) of lysine valproate are recovered.

EXAMPLE 4

To a solution of 18.6 g of lysine carbonate in a mixture of 20 ml of water and 25 ml of methanol 15.84 g of valproic acid are added by small portions. After stirring during about 1 hour, the clear solution obtained is filtered and evaporated under vacuum. The solid residue dissolved in 50 ml of methanol is added slowly to 250 ml of ethyl acetate under vigorous stirring. The lysine salt cristallizes out as a white powder which is filtered off. The obtained lysine valproate is instantaneously water-soluble.

The water-soluble valproic acid salts of the present invention exert a remarkable anticonvulsant activity.

The salts based on valproic acid of the invention may be administered in association with various pharmaceutical excipients, such as diluents, gelling agents, preservative agents, emulsifiers, sweetening agents and flavouring agents, etc., orally, parentally or rectally.

For oral administration, dragees, granules, lozenges (pellets), tablets, capsules, compressed tablets, solutions, syrups, emulsions, emulsions containing traditional additives or excipients in galenic industry are used.

These galenical forms may release the active agent in a normal or a time-programmed way.

For parental administration, any suitable vehicle will be used, such as, for example, sterile water, peanut oil or ethyl oleate.

For rectal administration, suppositories, rectal capsules, solutions or gels will be used.

The active compound may be administered alone or in combination with other active products having a similar or different activity.

The recommended doses are, for example, 100 mg to 6 g, advantageously 1 g to 3 g per day orally, rectally and intravenously.

Some examples for preparing solid forms containing as active agents one of the compounds according to the invention are given hereinafter.

EXAMPLE 1

(a) Formulation for one tablet.

| | |
|---|---|
| Valproic acid (lysine salt) | 800 mg |
| Polymethacrylate | 25 mg |
| Magnesium stearate | 1 mg |
| Ethyl acetate | sufficient amount |
| | 826 mg |

(b) Process of preparation.
1. Lysine salt of valproic acid and polymethylacrylate are granulated together with ethyl acetate, then screened and dried.
2. The magnesium stearate is admixed.
3. The product is pressed in tablets of 0.826 g each.

EXAMPLE 2

(a) Formulation for a dose of microgranules

| | |
|---|---|
| Valproic acid (lysine salt) | 800 mg |
| Hydroxypropylmethylcellulose | 200 mg |
| Shellac | sufficient amount |
| Ethyl alcohol | sufficient amount |

(b) Process of preparation.
1. Valproic acid (lysine salt) is granulated with a solution of hydroxypropylmethylcellulose in ethanol.
2. The granulated product is treated before drying by any suitable means in order to obtain more or less spherical microgranules.
3. Microgranules are dried and screened so as to select the wished diameter.
4. Shellac in alcoholic solution is sprayed on so obtained microgranules.
5. Microgranules are thoroughly dried, again screened and the kinetics of valproic acid liberation according to the desired type (delayed action, extended action and the like) is controlled.
6. So obtained microgranules are put into gelatin capsules.

It will be noted that a programmed liberation of the active substance may be obtained with other components than shellac, for example with ethylcellulose, cellulose acetophthalate, polymethacrylates. It is also obvious that use of these compounds is advisable when a delayed or programmed liberation of the active substance is desired; if a quick liberation has to be obtained, steps 4 and 5 can be deleted by passing from step 3 to step 6 directly.

It has to be noted that microgranules obtained as in example 2 may be presented as tablets, suspension, suppositories or any other pharmaceutically acceptable form, in addition to gelatin capsules.

Moreover, tablets obtained as in example 1 may be prepared so that the active substance liberation either is rapid or is delayed and/or extended. This will in particular be obtained by modifying relative amounts of methacrylic polymer and microcrystalline cellulose and/or by coating tablets as mentioned for microgranules in Example 2.

Studies of acute toxicity made orally on valproic acid lysine salt of example 1 have given following results, expressed as 50% lethal dose on animals.

Rats (both sexes): 2980 mg/kg of body weight (namely 1480 mg of pure valproic acid).

Mice (both sexes) : 2211 mg/kg for body weight (namely 1098 mg of pure valproic acid).

The data obtained with the substance according to the invention have shown a quick and substantial resorption.

Also, no delayed lethal effect is remarked, which also is a favourable element in this kind of study.

The substance administered to 12 healthy subjects gives identical valproic acid plasma levels to those obtained on these same subjects after administration of a similar dose of valproic acid sodium salt. However, the interindividual variations seem less important with the lysine salt than with the sodium salt.

I claim:

1. A water-soluble valproic acid salt useful as an anticonvulsant, which comprises the reaction product of valproic acid and a basic amino-acid selected from the group consisting of lysine and arginine.

2. A salt as claimed in claim 1, wherein the basic amino-acid is a levogyre amino-acid, a dextrogyre amino-acid or a mixture of said acids.

3. A salt as claimed in claim 1 which contains about 1 to 5 moles of basic amino-acid per mole of valproic acid.

4. A salt as claimed in claim 4, which contains about 1 mole of basic amino-acid per mole of valproic acid.

5. A pharmaceutical composition useful as an anticonvulsant and comprising as an active ingredient and effective amount of the water-soluble valproic acid salt of claim 1, and a suitable excipient.

6. A method treating a human host in need of anticonvulsant treatment, comprising administering to said host an effective amount of the valproic acid salt of claim 1.

7. The method of claim 6 wherein said administration is carried out orally, rectally or intravenously.

8. The method of claim 6 wherein said host is administered between 100 mg and 6 g of said salt daily.

9. A method of treating a human host in need of anticonvulsant treatment, comprising administering to said host an effective amount of the pharmaceutical composition of claim 5.

* * * * *